US012765851B2

(12) United States Patent
Sakaguchi

(10) Patent No.: US 12,765,851 B2
(45) Date of Patent: Oct. 20, 2026

(54) X-RAY DIAGNOSTIC APPARATUS AND CORRECTION METHOD

(71) Applicant: Canon Kabushiki Kaisha, Tokyo (JP)

(72) Inventor: Takuya Sakaguchi, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 145 days.

(21) Appl. No.: 18/949,498

(22) Filed: Nov. 15, 2024

(65) Prior Publication Data

US 2025/0160776 A1 May 22, 2025

(30) Foreign Application Priority Data

Nov. 17, 2023 (JP) ................................ 2023-196133

(51) Int. Cl.
*A61B 6/00* (2024.01)

(52) U.S. Cl.
CPC .................................. *A61B 6/481* (2013.01)

(58) Field of Classification Search
None
See application file for complete search history.

(56) References Cited

U.S. PATENT DOCUMENTS

2008/0107233 A1* 5/2008 Sakaguchi .......... A61B 6/4233 378/91
2014/0193099 A1* 7/2014 Yoshikawa .......... A61B 6/5235 382/295
2017/0161895 A1* 6/2017 Kowarschik ............. G06T 5/94

FOREIGN PATENT DOCUMENTS

JP 2005-295139 A 10/2005

* cited by examiner

*Primary Examiner* — Hoon K Song
(74) *Attorney, Agent, or Firm* — Oblon, McClelland, Maier & Neustadt, L.L.P.

(57) ABSTRACT

According to one embodiment, an X-ray diagnostic apparatus includes an X-ray tube, an X-ray detector, and processing circuitry. The X-ray tube radiates X-rays toward a subject into which a contrast medium is injected. The an X-ray detector detects the X-rays transmitted through the subject. The processing circuitry generates an X-ray image based on an output from the X-ray detector. The processing circuitry acquires indexes related to a brightness of the X-ray image. The processing circuitry corrects, based on a reference index prior to injection of the contrast medium and a latest index after start of the injection of the contrast medium, a brightness value of the X-ray image relative to the latest index, the reference index and the latest index being included in the acquired indexes.

12 Claims, 12 Drawing Sheets

X-RAY DIAGNOSTIC APPARATUS AND CORRECTION METHOD

CROSS-REFERENCE TO RELATED APPLICATION

This application is based upon and claims the benefit of priority from the prior Japanese Patent Application No. 2023-196133, filed Nov. 17, 2023, the entire contents of which are incorporated herein by reference.

FIELD

Embodiments described herein relate generally to an X-ray diagnostic apparatus and a correction method.

BACKGROUND

A myocardial blood flow measurement and analysis method, which uses X-ray images of a heart region into which a contrast medium has been injected, has been proposed. In this method, multiple-frame X-ray images are acquired by an X-ray diagnostic apparatus after the injection of the contrast medium, and image analysis is performed using an image density change of the X-ray image in a temporal direction. Such a method is based on the premise that the imaging conditions do not change in the temporal direction. This premise is provided in consideration of the fact that it becomes difficult to use the image density change caused by the contrast medium if the image density of the entire X-ray image changes with a change in the imaging conditions.

In everyday clinical practice, on the other hand, an X-ray diagnostic apparatus is often configured to change the imaging conditions in the temporal direction through execution of automatic brightness control, so as to brighten the entire X-ray image that has been darkened by injection of a contrast medium. In such a case, the image density change of the X-ray image is affected by the change in the imaging conditions, and it cannot be directly used for the image analysis.

It is therefore desirable to suppress, in the image density change of the X-ray image in the temporal direction caused by the contrast medium, the effect caused by the change in the imaging conditions.

DETAILED DESCRIPTION

In general, according to one embodiment, an X-ray diagnostic apparatus includes an X-ray tube, an X-ray detector, and processing circuitry. The X-ray tube is configured to radiate X-rays toward a subject into which a contrast medium is injected. The X-ray detector is configured to detect the X-rays radiated by the X-ray tube and transmitted through the subject. The processing circuitry is configured to generate an X-ray image based on an output from the X-ray detector. The processing circuitry is configured to acquire indexes related to a brightness of the X-ray image. The processing circuitry is configured to correct, based on a reference index prior to injection of the contrast medium and a latest index after start of the injection of the contrast medium, a brightness value of the X-ray image relative to the latest index, the reference index and the latest index being included in the acquired indexes.

Now, an X-ray diagnostic apparatus and a correction method according to the embodiments will be described with reference to the drawings. First, the terms to be used herein will be defined as follows. A pulse rate is an index defining a frequency at which X-rays are radiated toward a subject, and represents the number of X-ray radiations per unit time (one second or minute) or per heartbeat in units (the number of times per second or minute, or the number of times per heartbeat). The frame rate representing the number of images taken per unit time is substantially equivalent to the pulse rate. The case where X-rays defined by the pulse rate are radiated includes not only an aspect in which X-rays of the pulse rate are generated from an X-ray tube and are directly radiated toward the subject, but also an aspect in which X-rays are continuously generated, and X-rays defined by the pulse rate are formed by an X-ray shutter, etc. and are radiated toward the subject. The term "perfusion" refers to delivery of blood to the cardiac muscle. An "R wave" represents a peak wave of the electrocardiographic waveform. An "RR interval" represents a time interval between two R waves. A tube current flowing between the electrodes of the X-ray tube is expressed by "mA", which is used as an index indicating a height of the pulse X-rays. A "pulse width" represents a duration of X-rays of a single pulse, expressed in units of "msec". A tube current-time product obtained by multiplying a tube current by a pulse width is expressed by "mAs", which is used as an index indicating an intensity of X-rays. In the description that follows, structural components having substantially the same function and configuration will be assigned the same symbol to omit a repetitive description thereof.

First Embodiment

Figure 1:
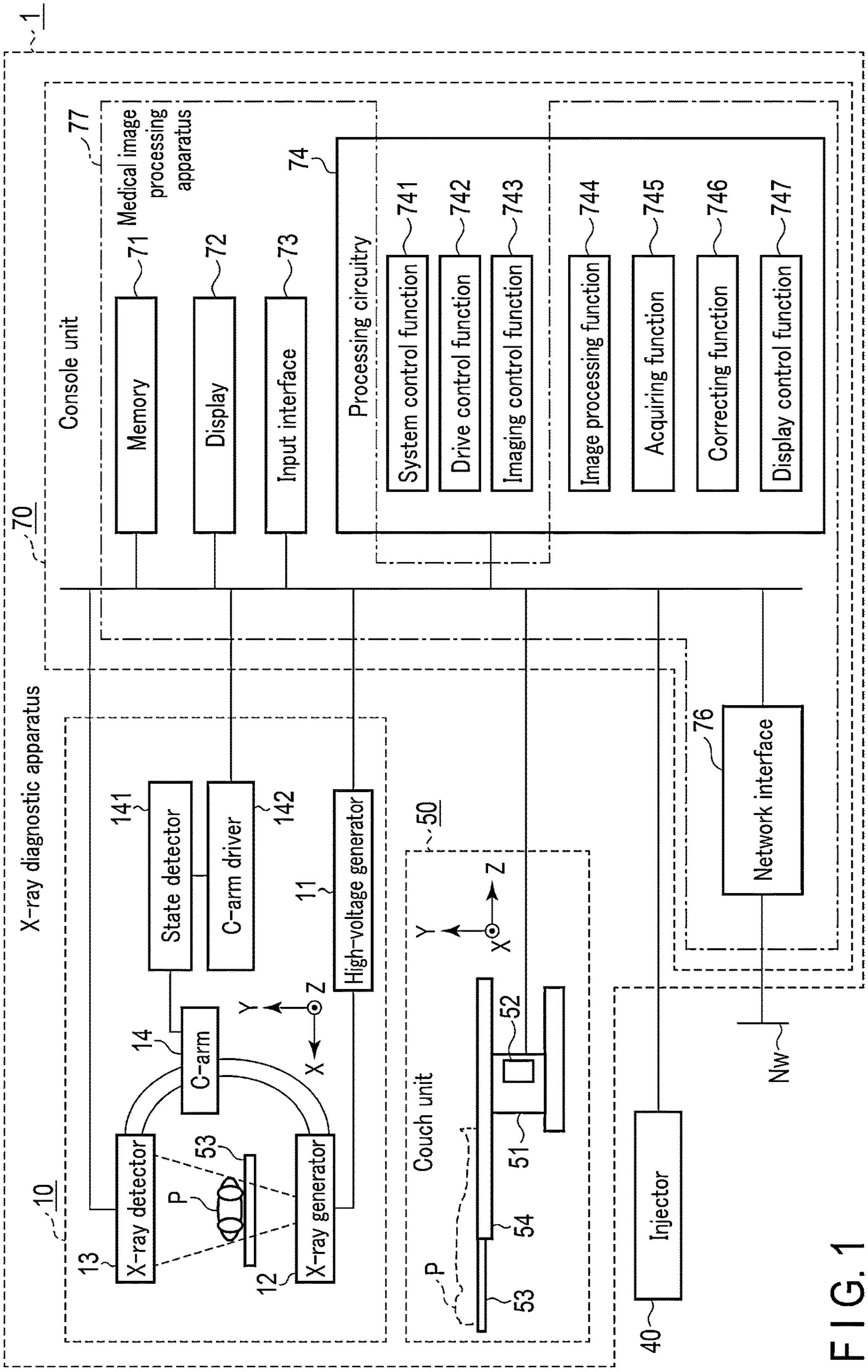
FIG. 1 is a block diagram showing a configuration example of an X-ray diagnostic apparatus according to a first embodiment.

FIG. 1 is a block diagram showing a configuration example of an X-ray diagnostic apparatus 1 according to a first embodiment. The X-ray diagnostic apparatus 1 includes an imaging unit 10, an injector 40, a couch unit 50, and a console unit 70. The imaging unit 10 includes a high-voltage generator 11, an X-ray generator 12, an X-ray detector 13, a C-arm 14, a state detector 141, and a C-arm driver 142.

The high-voltage generator 11 is adapted to generate and output high voltages to an X-ray tube so that the high voltages are applied between an anode and a cathode of the X-ray tube in order to accelerate thermal electrons produced from the cathode.

The X-ray generator 12 is provided with this X-ray tube for radiating X-rays toward a subject P, and also an X-ray diaphragm having functions of delimiting the radiation field of the X-rays, attenuating the X-rays for a portion of the radiation fields, and so on.

The X-ray tube is adapted to generate X-rays. More specifically, the X-ray tube is a vacuum tube having a cathode for producing thermal electrons and an anode for receiving the thermal electrons flying from the cathode to generate X-rays. Examples of the X-ray tube include an X-ray tube of a rotating anode type, which generates X-rays by emitting thermal electrons to a rotating anode. The X-ray tube is connected to the high-voltage generator 11 through a high-voltage cable. The high-voltage generator 11 applies a tube voltage between the cathode and the anode. Upon this tube voltage application, thermal electrons fly from the cathode toward the anode. As the thermal electrons fly from the cathode toward the anode, a tube current flows. Thus, with the application of high voltage and the supply of filament current from the high-voltage generator 11, thermal electrons fly from the cathode to the anode and collide with the cathode, thereby generating X-rays.

The X-ray diaphragm, which is arranged between the X-ray tube and the X-ray detector 13, typically employs diaphragm blades, as well as an added filter and a compensating filter. The X-ray diaphragm is adapted to limit the X-rays generated by the X-ray tube by blocking the X-ray paths except the area of opening so that the X-rays will be applied only to a region of interest of the subject P. For example, the X-ray diaphragm includes four diaphragm blades each constituted by a lead plate, and by sliding these diaphragm blades the X-ray shield area can be adjusted into a desired size. The diaphragm blades of the X-ray diaphragm may be driven by a driver (not illustrated) according to the region of interest input by an operator via an input interface 73. The X-ray diaphragm also has a slit that can receive insertion of an added filter for adjusting the total filtration of X-rays. The X-ray diaphragm further has an accessory slot that can receive insertion of a lead mask or a compensating filter for use during X-ray inspection operations. The compensating filter may include a region-of-interest (ROI) filter having a function of attenuating or reducing the amount of X-ray radiation.

The X-ray detector 13 is adapted to detect X-rays radiated by the X-ray tube and transmitted through the subject P. This X-ray detector 13 may be a type that converts X-rays directly into electric charges, or a type that first converts X-rays into light and then converts the light into electric charges. The description will assume the former type, but the X-ray detector 13 may also be the latter type. Specifically, and for example, the X-ray detector 13 includes a planar, flat panel detector (FPD) for converting the X-rays transmitted through the subject P into electric charges to accumulate, and a gate driver for generating drive pulses for reading the electric charges accumulated in the FPD. The FPD includes micro sensor elements arranged two-dimensionally in a column direction and a line direction. The sensor elements each include a photoelectric film, a charge accumulation capacitor, and a thin film transistor (TFT). The photoelectric film senses X-rays and generates electric charges according to the amount of incident X-rays. The charge accumulation capacitor accumulates the electric charges generated at the photoelectric film. The TFT outputs, at predetermined timings, the electric charges accumulated at the charge accumulation capacitor. The accumulated electric charges are sequentially read with the drive pulses supplied from the gate driver.

While not illustrated, there are projection data generation circuitry and projection data storage circuitry arranged in the back part of the X-ray detector 13. The projection data generation circuitry includes a charge-voltage converter, an analog-digital (A/D) converter, and a parallel-serial converter. The charge-voltage converter converts the electric charges, read in units of rows or columns in a parallel manner from the FPD, into voltages. The A/D converter converts the output of this charge-voltage converter into digital signals. The parallel-serial converter converts the digitally converted parallel signals into time-series serial signals. The projection data generation circuitry supplies these serial signals to the projection data storage circuitry as time-series projection data. The projection data storage circuitry sequentially stores the time-series projection data supplied from the projection data generation circuitry so that two-dimensional projection data is generated. The two-dimensional projection data is output to the console unit 70 as a detection result of the X-rays, and then stored in a memory 71.

The C-arm 14 is adapted to hold the X-ray generator 12 and the X-ray detector 13 in such a manner that they face each other with the subject P and a couch top 53 arranged therebetween, so that X-ray imaging of the subject P placed on the couch top 53 is enabled. By way of example, the following description will assume the C-arm 14 to be a type that is suspended from the ceiling; however, the configuration is not limited thereto, and the C-arm 14 may be, for example, a floor-mounted type.

As a more specific configuration, the C-arm 14 is adapted to be movable along the directions of the long axis and the short axis of the couch top 53. The C-arm 14 is supported by a support arm via a holding portion. The support arm is of a substantially arc shape and has a proximal end attached to a movement mechanism for a rail installation on the ceiling. The C-arm 14 is held by the holding portion so as to be rotatable about an axis extending in an X direction orthogonal to both a Y direction perpendicular to the couch top 53 and a Z direction along the long axis of the couch top 53. The C-arm 14 is of a substantially arc shape, which is concentric on the Z-direction axis, and held by the holding portion so as to be slidable along the substantially arc shape. That is, the C-arm 14 is also capable of a sliding movement about the Z-direction axis. The C-arm 14, with the capability of said rotational movement about the X-direction axis through the holding portion ("main rotational movement") in combination with this sliding movement, can enable X-ray image observations at various angles and from various directions. The C-arm 14 may further be rotatable about the Y-direction axis whereby the center of the sliding movement coincides with, for example, the X-direction axis. Note that the focal point of the X-rays from the X-ray generator 12 and the imaging axis extending through the center of the X-ray detector 13's detection plane are designed to intersect each other at a single point that is on the axis as the center of the sliding movement and also on the axis as the center of the main rotational movement. Such a point of intersection is generally called an "isocenter". The isocenter is not displaced with the sliding movement or the main rotational movement of the C-arm 14. As such, once a concerned site is positioned at the isocenter, observation of the site through the moving medical images acquired from the C-arm 14's slicing movement or main rotational movement will be facilitated.

For the C-arm 14 of this configuration, multiple power sources are provided at suitable, applicable locations in order to realize the operations of the support arm under the rail installation, or the operations in the X-direction axis, the Y-direction axis, and the Z-direction axis. These power sources constitute the C-arm driver 142. The C-arm driver 142 reads drive signals from a drive control function 742 to cause the C-arm 14 to perform sliding movement, rotational movement, linear movement, etc. The C-arm 14 is also provided with the state detector 141 for detecting each piece of information about the angle or orientation, position, etc. of the C-arm 14. The state detector 141 includes, for example, a potentiometer for detecting a rotation angle, a movement amount, etc., an encoder as a position sensor, and so on. Examples of the available encoder includes a so-called absolute encoder of a magnetic type, a brush type, a photoelectric type, or the like. As the state detector 141, various position detecting mechanisms may also be discretionarily adopted, such as a rotary encoder outputting rotational displacement in the form of digital signals, or a linear encoder outputting linear displacement in the form of digital signals.

The injector 40 is adapted to inject a contrast medium to the subject P according to the injection amount and the injection rate communicated from an imaging control function 743, at the time of taking a contrast-enhanced blood vessel X-ray image of the subject P.

The couch unit 50 is a unit adapted to movably carry the subject P, and includes a base 51, a couch driver 52, the couch top 53, and a support frame 54.

The base 51 is a housing on the floor, and is adapted to support the support frame 54 in such a manner that the support frame 54 can move vertically (in the Y direction).

The couch driver 52 may be disposed in the housing of the couch unit 50, and includes a motor or an actuator adapted to move the top 53, on which the subject P is placed, in the longitudinal direction of the couch top 53 (in the Z direction). The couch driver 52 reads drive signals from the drive control function 742 to cause the couch top 53 to move horizontally or vertically with respect to the floor face.

The couch top 53 is provided on the upper side of the support frame 54, and may be a plate adapted for placement of the subject P.

The support frame 54 is adapted to support the couch top 53 so that the couch top 53, on which the subject P is placed, can move. More specifically, the support frame 54 is provided at the upper portion of the base 51, and supports the couch top 53 so that the couch top 53 can slide in its longitudinal direction.

The console unit 70 includes the memory 71 and input interface 73, as well as a display 72, processing circuitry 74, and a network interface 76.

The memory 71 is a storage device configured to store various types of information, such as a read-only memory (ROM), random-access memory (RAN), a hard disk drive (HDD), a solid-state drive (SSD), etc. The memory 71 may be a drive assembly configured to read and write various types of information from and into portable storage media such as a CD-ROM drive, a DVD drive, a flash memory, etc. Note that the memory 71 is not necessarily be implemented by a single storage device. For example, the memory 71 may be implemented by a plurality of storage devices. Also, the memory 71 may be in another computer connected to the X-ray diagnostic apparatus 1 via a network Nw.

The memory 71 stores various programs such as processing programs of the X-ray diagnostic apparatus 1, as well as various types of data such as various types of information to be used for processing, data being processed, and data that has been processed. The processing programs may be, for example, stored in advance in the memory 71. Also, the processing programs may be, for example, stored in a non-transitory computer-readable storage medium and distributed, read from the non-transitory computer-readable storage medium, and installed in the memory 71. Examples of the various types of data include projection data prior to image processing, and medical images such as X-ray images subjected to image processing and contrast images. A contrast image is an X-ray image acquired by imaging a subject's heart region with a contrast medium injected. The X-rays radiated from the X-ray tube largely change their intensity in the course of passing through the contrast medium present in the subject's heart region, and then enter the X-ray detector 13. In a contrast image, accordingly, the blood vessels and the cardiac muscle in the subject's heart region appear together with a background such as the subject's bone.

Of the functions and indexes for acquiring indexes related to a brightness of the X-ray image, for example, a program causes a computer to realize the function of correcting, based on a reference index prior to injection of a contrast medium and a latest index after start of the injection, a brightness value of the X-ray image relative to the latest index. Note that such a program may be installed in advance in the computer from, for example, a network or a non-transitory computer-readable storage medium, so that the computer realizes each function of an internal medical image processing apparatus 77. The memory 71 is one example of a storage.

The display 72 includes a display main part for displaying various information including the medical images, etc., internal circuitry for supplying signals for display to the display main part, and peripheral circuitry including connectors, cables, or the like for connection between the display main part and the internal circuitry. The internal circuitry is adapted to generate display data by superimposing supplemental information, such as subject information and projection data generation conditions, on the image data given from the processing circuitry 74, and to subject the display data to D/A conversion and TV format conversion for display through the display main part. For example, the display 72 outputs medical images generated by the processing circuitry 74, graphical user interfaces (GUI's) for accepting various operations from an operator, and so on. For example, the display 72 may be a liquid crystal display or a cathode ray tube (CRT) display. The display 72 is one example of a display. Also, the display 72 may be a desktop type, or implemented as a tablet terminal, etc. capable of wireless communications with the main part of the console unit 70. The display 72 is another example of the display.

The input interface 73 enables input of subject information, setting of imaging conditions, input of various command signals, and so on. The subject information includes, for example, a subject ID, as well as a subject's name, date of birth, age, weight, gender, site for inspection, etc. Note that the imaging conditions include X-ray conditions. The input interface 73 is connected to an input device for providing, for example, instructions for movement of the C-arm 14, setting of a region of interest (ROI), etc., and such components include a trackball, switch buttons, a mouse, a keyboard, a touch pad which allows an input operation through contacting the operation screen, and a touch panel which integrates a display screen and a touch pad. The input device connected to the input interface 73 may be an input device provided in another computer connected via a network Nw, etc. The input interface 73, which is connected to the processing circuitry 74, converts input operations received from operators into electric signals, and outputs the electric signals to the processing circuitry 74. The input interface 73 may instead be implemented as a tablet terminal, etc., capable of wireless communications with the main part of the console unit 70. In the present disclosure, the input interface 73 is not limited to physical operating components such as a mouse and a keyboard. That is, the examples of the input interface 73 also include processing circuitry for electrical signals that is adapted to receive an electrical signal corresponding to an input operation from an external input device separate from the apparatus, and to output this electrical signal to the processing circuitry 74.

The processing circuitry 74 controls the operations of the entire X-ray diagnostic apparatus 1 in accordance with an electric signal of an input operation output from the input interface 73. As hardware resources, the processing circuitry 74 includes, for example, processors such as a CPU, an MPU, and a graphics processing unit (GPU), and memories such as a ROM and a RAM. The processing circuitry 74 is a processor adapted to read and execute programs in the memory 71 for realizing functions corresponding to the programs, including a system control function 741, the drive control function 742, the imaging control function 743, an image processing function 744, an acquiring function 745, a correcting function 746, and a display control function 747. While FIG. 1 assumes that the processing circuitry 74 is a single circuitry element for realizing the system control function 741, the drive control function 742, the imaging control function 743, the image processing function 744, the acquiring function 745, the correcting function 746, and the display control function 747, the processing circuitry 74 may be constituted by a combination of multiple independent processors each running a program to realize the respective function. Also, the system control function 741, the drive control function 742, the imaging control function 743, the image processing function 744, the acquiring function 745, the correcting function 746, and the display control function 747 may be called a system control circuit, a drive control circuit, an imaging control circuit, an image processing circuit, an acquiring circuit, a correcting circuit, and a display control circuit, respectively, and they may be implemented as individual hardware circuits.

The system control function 741, for example, handles information, such as command signals or various initial setting conditions input via the input interface 73 by an operator, in such a manner that it temporarily holds the information and then sends the information to respective, corresponding processing functions of the processing circuitry 74.

The drive control function 742, for example, controls the C-arm driver 142 and the couch driver 52 using information input via the input interface 73 in relation to driving of the C-arm 14 and the couch top 53. For example, the drive control function 742 controls the movement and rotation in the imaging unit 10, the movement and tilt in the couch unit 50, etc.

The imaging control function 743, for example, controls imaging conditions (X-ray conditions) including a tube voltage from the high-voltage generator 11, a tube current, a pulse width, a pulse rate, a radiation time, etc., upon reading the information from the system control function 741. The imaging conditions may include a tube current-time product (mAs) obtained by multiplying the tube current by the pulse width. Also, the imaging control function 743 may perform automatic brightness control (ABC) for optimizing the brightness of the X-ray image. In the automatic brightness control, the imaging conditions (X-ray conditions) are controlled in such a manner that a brightness value of the current X-ray image is adjusted to a set value. As the brightness value of the current X-ray image, a value obtained by, for example, taking an average of brightness values acquired from a part or the entirety of the X-ray image can be used. With the automatic brightness control, it is possible to brighten the entire X-ray image by changing the imaging conditions if, for example, the entire X-ray image has been darkened through injection of the contrast medium. In the case of changing the imaging conditions, it is preferable that the tube current-time product (mAs) be changed, with the tube voltage fixed. In the case of changing the tube current-time product, it suffices that at least one of the tube current and the pulse width be changed. Also, the imaging control function 743 may perform control of the imaging conditions such as the pulse rate based on an injection start signal output from the injector 40 at the start of injection of a contrast medium into the subject P from the injector 40 to the subject P and an injection completion signal output from the injector 40 upon completion of the injection of the contrast medium into the subject P, and an electrocardiogram (ECG) of the subject P measured by an electrocardiograph (not illustrated). The imaging control function 743 and the processing circuitry 74 are examples of an imaging controller configured to perform automatic brightness control, which controls brightness of an X-ray image of the subject P through adjustment of the imaging conditions of the X-ray image.

The image processing function 744, for example, generates an X-ray image by subjecting projection data in the memory 71 to image processing such as filtering, and stores the X-ray image in the memory 71. Examples of the X-ray image generated from the projection data include an X-ray image prior to injection of the contrast medium, and a medical image such as an X-ray image (a contrast image) after the start of injection of the contrast medium. The image processing function 744 and the processing circuitry 74 are examples of an image generator configured to generate an X-ray image of the subject P based on an output (a detection result) from the X-ray detector 13. Also, the image processing function 744 and the processing circuitry 74 are examples of an image generator configured to sequentially generate multiple-frame X-ray images in chronological order based on an output from the X-ray detector 13.

The acquiring function 745 acquires indexes related to the brightness of the X-ray image. The acquiring function 745 may acquire, for example, such indexes for each frame of the X-ray image. Moreover, the acquiring function 745 may acquire, for example, imaging conditions of the X-ray image as the indexes. Furthermore, the acquiring function 745 may acquire a tube current-time product as one of the indexes. The acquiring function 745 and the processing circuitry 74 are examples of an acquiring unit.

Of the indexes acquired by the acquiring function 745, the correcting function 746 corrects, based on a reference index prior to injection of a contrast medium and a latest index after start of the injection of the contrast medium, a brightness value of the X-ray image relative to the latest index. The correcting function 746 may, for example, correct the brightness value so as to maintain the brightness of the X-ray image relative to the reference index. Maintaining the brightness means making the brightness substantially constant. Also, the correcting function 746 may, for example, obtain a change ratio of the latest index to the reference index, and correct the brightness value based on the change ratio. The change ratio may be obtained either by calculation or by referring to a table in which the values of the reference index, the latest index, and the change ratio are associated. The correcting function 746 and the processing circuitry 74 are examples of a correcting unit.

The display control function 747, for example, performs control for causing the display 72 to present display data such as medical images stored in the memory 71. For example, the control, etc. performed by the display control function 747 includes reading signals from the system control function 741, acquiring a desired X-ray image from the memory 71, and displaying it on the display 72. The display control function 747 and the processing circuitry 74 are examples of a display controller configured to cause a display to display an X-ray image with a brightness value that has been corrected by the correcting function 746.

The network interface 76 is circuitry for connecting the console unit 70 to the network Nw for communications with other entities or apparatuses such as an external medical image processing apparatus. As the network interface 76, for example, a network interface card (NIC) may be adopted. In the following disclosure, such a description as the network interface 76 being involved in the communications with other entities or apparatuses will be omitted.

The memory 71, the display 72, the input interface 73, and the processing circuitry 74 with the image processing function 744, the acquiring function 745, the correcting function 746, and the display control function 747 as described above together constitute the medical image processing apparatus 77. Accordingly, the explanations of the memory 71, the display 72, and the input interface 73, as well as the image processing function 744, the acquiring function 745, the correcting function 746, and the display control function 747 of the processing circuitry 74 should be understood as explanations of the respective features in the X-ray diagnostic apparatus 1 and the medical image processing apparatus 77. The medical image processing apparatus 77 may be provided within the X-ray diagnostic apparatus 1, or may be provided as a discrete apparatus outside the X-ray diagnostic apparatus 1.

Figure 2:
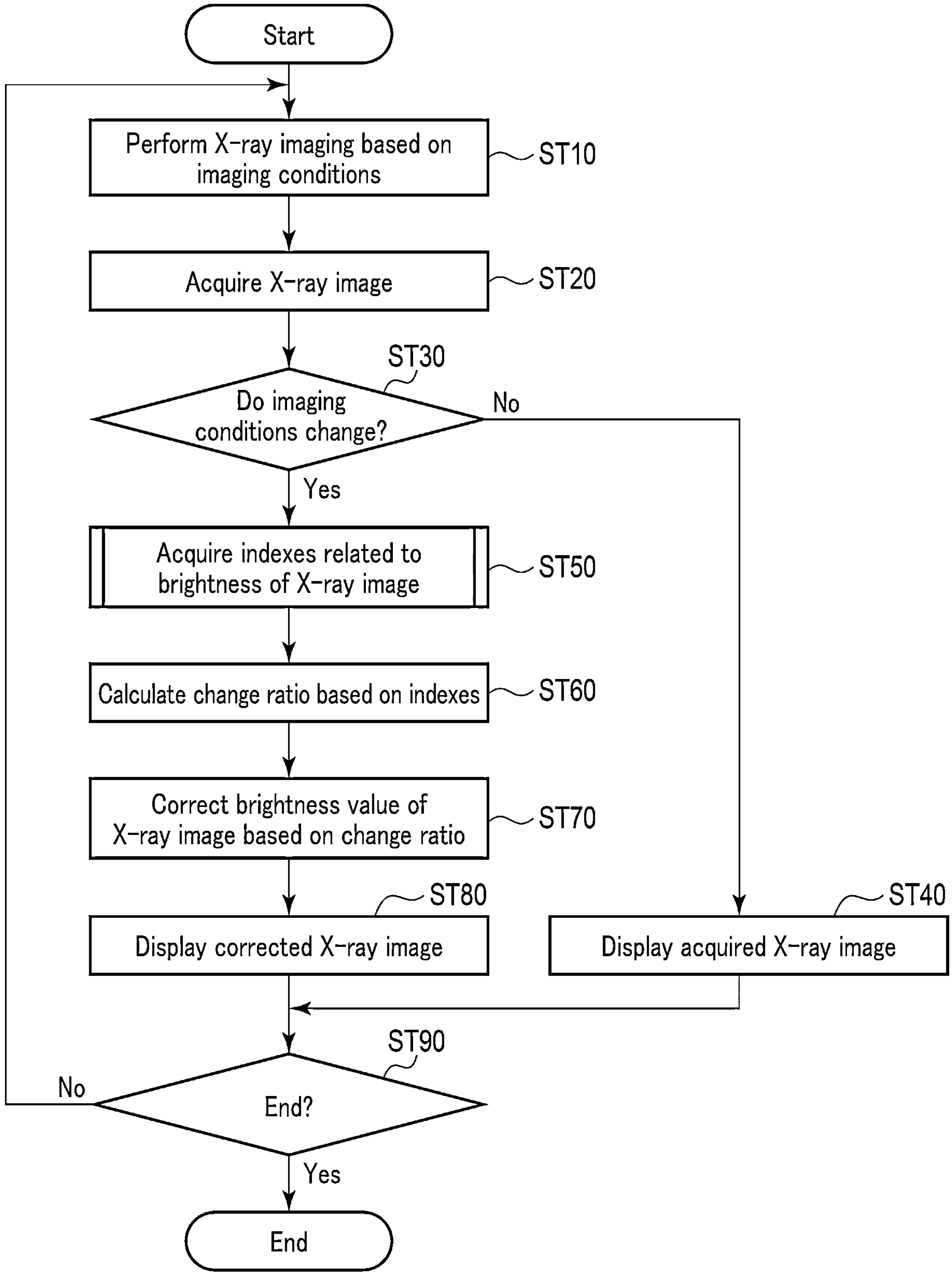
FIG. 2 is a flowchart for illustrating operations in the first embodiment.
Figure 4:
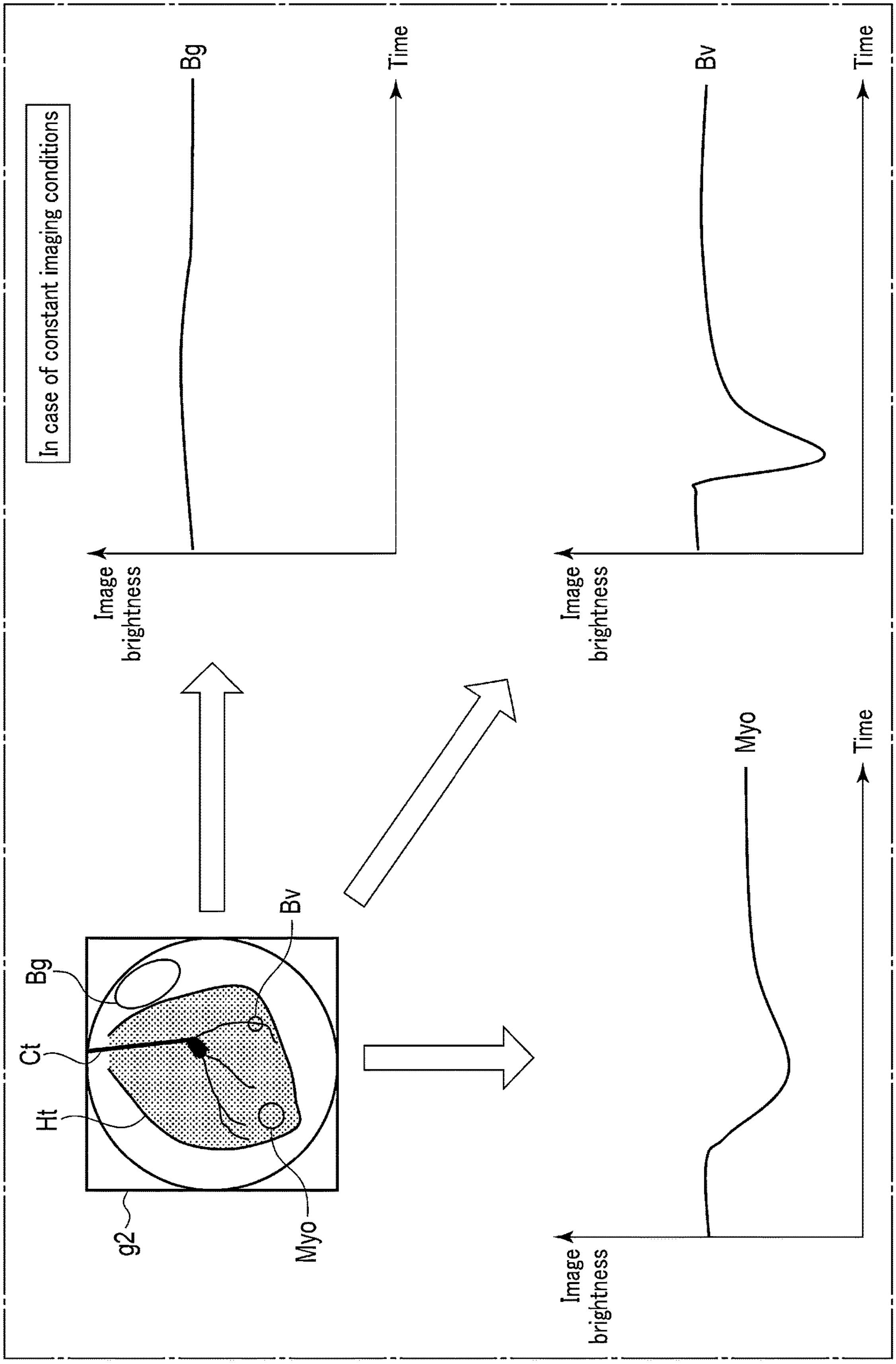
FIG. 4 is a schematic diagram for illustrating an image brightness in a case where imaging conditions are constant.
Figure 5:
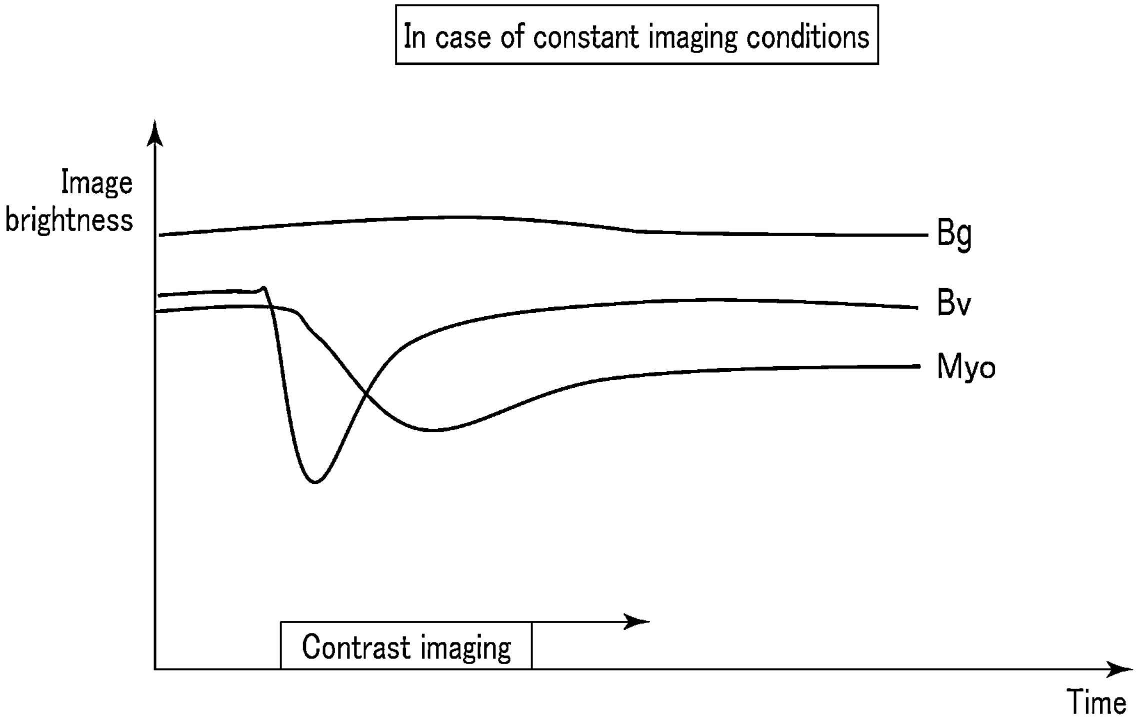
FIG. 5 is a schematic diagram for illustrating an image brightness in a case where imaging conditions are constant.
Figure 6:
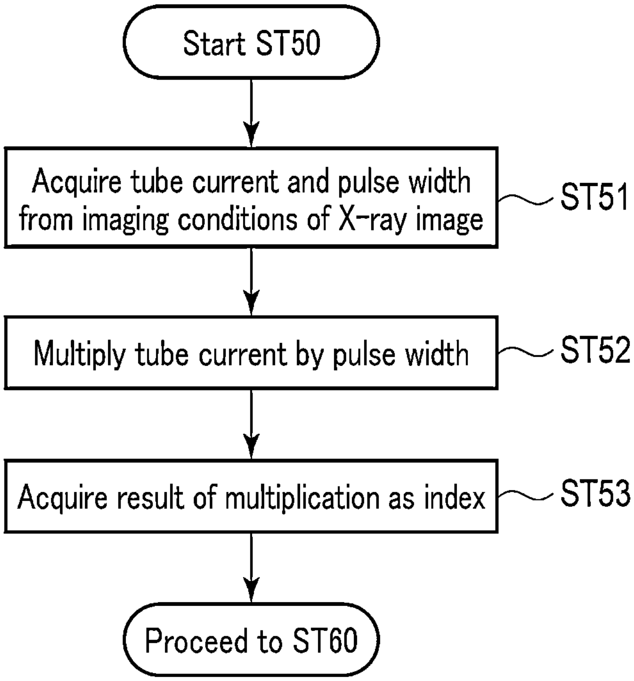
FIG. 6 is a flowchart for illustrating operations at step ST50 in FIG. 2.

Now, how the X-ray diagnostic apparatus configured as above operates will be described with reference to FIGS. 2 to 8. FIGS. 2 and 6 show flowcharts, and FIGS. 3 to 5, 7, and 8 show schematic diagrams. It is assumed that the subject P is placed on the couch top 53, and that a catheter is inserted into the coronary artery of the heart through X-ray imaging (fluoroscopic imaging). In the first embodiment, after low-dose preliminary contrast imaging (ST10-ST40 and ST90) for manually setting a region of interest, main contrast imaging for performing image analysis including creation of a time density curve is performed (ST10-ST30 and ST50-ST90). At this point in time, however, a contrast medium has not been injected into the subject P.

As shown in FIG. 2, at step ST10, the X-ray diagnostic apparatus 1 performs X-ray imaging based on the imaging conditions. That is, an X-ray tube radiates X-rays toward the subject P into which a contrast medium is injected. The X-ray detector 13 is adapted to detect X-rays radiated from the X-ray tube and transmitted through the subject P, and to output a detection result of the X-rays. The processing circuitry 74 generates an X-ray image of the subject P based on an output from the X-ray detector 13, and stores the X-ray image in the memory 71.

At step ST20, the processing circuitry 74 acquires an X-ray image from the memory 71.

At step ST30, the processing circuitry 74 determines whether or not the imaging conditions of the X-ray image change according to, for example, whether or not automatic brightness control is in an on-state; if not, the processing shifts to step ST40. The case where the result of the determination at step ST30 is no (ST30; No) corresponds to an off-state of the automatic brightness control. The case where the processing shifts to step ST40 after the processing at steps ST10 to ST30 corresponds to the preliminary contrast imaging for setting a region of interest.

At step ST40, the processing circuitry 74 causes the display 72 to display an X-ray image acquired at step ST20, and shifts to step ST90.

At step ST90, the processing circuitry 74 determines whether or not contrast imaging of the subject P's heart region has been complete; if not, the processing returns to step ST10.

Figure 3:
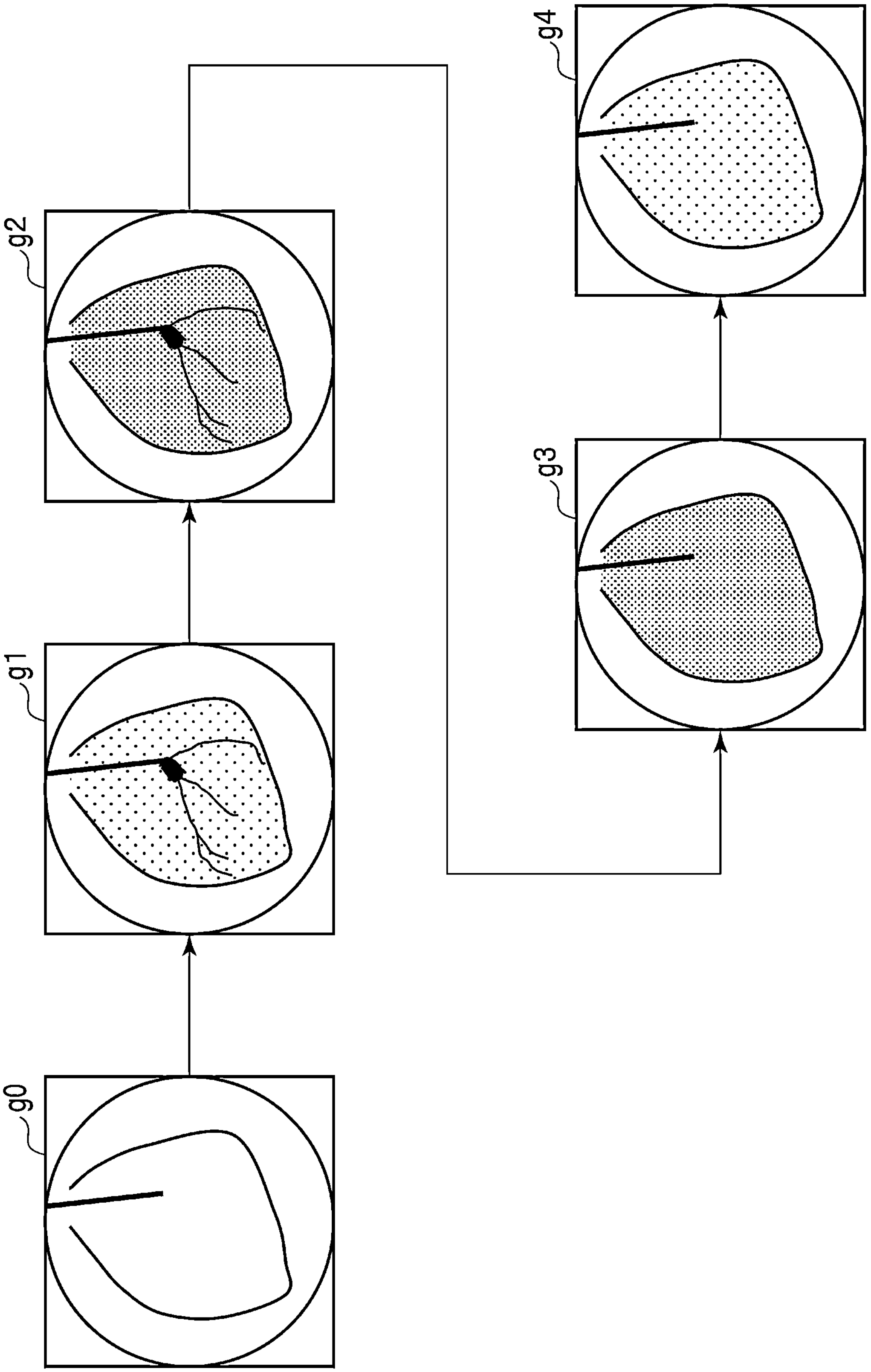
FIG. 3 is a schematic diagram for illustrating operations in the first embodiment.

That is, if the automatic brightness control is in the off-state, the X-ray diagnostic apparatus 1 repeatedly performs the operations from step ST10 to step ST40 via step ST90 during the low-dose preliminary contrast imaging in which the imaging conditions do not change. Through such contrast imaging, multiple-frame X-ray images g0, . . . , g1, . . . , g2, . . . , g3, . . . , and g4, . . . are sequentially acquired by the processing circuitry 74 along the time direction, as shown in FIG. 3, and are displayed on the display 72. The X-ray image g0 shown in FIG. 3 is an image acquired prior to the contrast imaging, in which a catheter inserted into the coronary artery is observed. The X-ray image g1 is an image acquired at the start of contrast imaging, in which blood vessels and cardiac muscles with a low concentration of the contrast medium are observed via a contrast medium injected from the catheter and reaching the cardiac muscles through blood. The X-ray image g2 is an image acquired at the middle stage of the contrast imaging, in which blood vessels and cardiac muscles with a high concentration of the contrast medium are observed. The X-ray image g3 is an image acquired upon completion of the contrast imaging, in which cardiac muscles with a high density of the contrast medium are observed as a result of occurrence of cardiac-muscle perfusion, in which the contrast medium flows from the blood vessels to the cardiac muscles. The X-ray image g4 is an image acquired after the completion of the contrast imaging, in which cardiac muscles with a low density of the contrast medium are observed as a result of the contrast medium not fully flowing from the cardiac muscles.

Each of such X-ray images includes a contrast region which a contrast medium reaches during the contrast imaging, and a background region which a contrast medium does not reach during the contrast imaging. The X-ray image g2 includes a heart region Ht, which is a contrast region, and a background region, which is a region other than the heart region Ht, as shown, for example, in the upper left of FIG. 4. The heart region Ht includes a blood vessel region and a cardiac muscle region. The catheter Ct is inserted into the blood vessels. These regions are located at similar positions in the other X-ray images g0, . . . , g1, . . . , g3, . . . , g4, . . . . After the low-dose preliminary contrast imaging, a background region of interest Bg is set in a part of the background region in accordance with an operation of the input interface 73 by the operator through observation of the X-ray images g0, . . . , g1, . . . , g2, . . . , g3, . . . g4, . . . . Similarly, a blood-vessel region of interest By is set in a part of the blood vessel region, and a cardiac-muscle region of interest Myo is set in a part of the cardiac muscle region. In the background region of interest Bg, which the contrast medium does not reach, the image brightness is substantially constant if the imaging conditions are constant, as shown in the upper right of FIG. 4. In the blood-vessel region of interest Bv, through which the contrast medium flows, the image brightness suddenly decreases after the start of the contrast imaging, and gradually recovers toward the end of the contrast imaging, as shown in the lower right of FIG. 4. In the cardiac-muscle region of interest Myo, which the contrast medium reaches from the blood vessels, the image brightness gradually decreases after the start of the contrast imaging, and gradually recovers toward the end of the contrast imaging, as shown in the lower left of FIG. 4. That is, if the imaging conditions are constant (ST30; No), the image brightness during the contrast imaging in each of the background region of interest Bg, the blood-vessel region of interest Bv, and the cardiac-muscle region of interest Myo progresses as shown in FIG. 5.

On the other hand, if the imaging conditions are determined to change at step ST30, the processing circuitry 74 shifts to step ST50. The case where the imaging conditions are determined at step ST30 to change (ST30; Yes) corresponds to the on-state of the automatic brightness control. The case where the processing shifts to step ST50 after the operations at steps ST10 to ST30 corresponds to the main contrast imaging after the preliminary contrast imaging.

At step ST50, the processing circuitry 74 acquires, for example, indexes related to the brightness of the X-ray image for each frame of the X-ray image. Step ST50 includes steps ST51 to ST53, as shown, for example, in FIG. 6. That is, the processing circuitry 74 refers to the memory 71, and acquires a tube current and a pulse width from the imaging conditions of the X-ray image (ST51). Also, the processing circuitry 74 multiples the acquired tube current by the pulse width (ST52), and acquires a result of the multiplication, which is a tube current-time product, as one of the indexes (ST53). Step ST50 is complete upon performing such steps.

At step ST60, of the acquired indexes, the processing circuitry 74 calculates, based on a reference index prior to injection of a contrast medium and a latest index after start of injection of the contrast medium, a change ratio of the latest index to the reference index. If, for example, the reference index is Id0 and the latest index is Idn, the processing circuitry 74 calculates a change ratio k from the formula: k=Idn/Id0. Note that the reference index Id0 is a reference tube current-time product prior to the injection of the contrast medium, and the latest index Idn is a latest tube current-time product after the start of the injection of the contrast medium. The tube current-time product is an example of the indexes related to the brightness of the X-ray image. The greater the tube current-time product is, the brighter the X-ray image becomes. The change ratio k is updated, for each frame of the X-ray image, to a value that varies according to a change in the latest tube current-time product. If, for example, the change ratio k=1.1, the latest X-ray image is 1.1 times as bright as the reference X-ray image.

At step ST70, the processing circuitry 74 corrects the brightness value of the X-ray image relative to the latest index Idn based on the change ratio. If, for example, the brightness value of the X-ray image relative to the latest index Idn is Bn, the processing circuitry 74 calculates the corrected brightness value Cn from the formula: Cn=Bn/k. If, for example, the change ratio k=1.1, the corrected brightness value Cn becomes approximately 0.91 times as great as the corrected brightness value Bn. The formula for obtaining the corrected brightness value Cn is calculated from the relationship of Id0:Idn=Cn:Bn (Cn=Bn(Id0/Idn)=Bn/k). Thereafter, the processing circuitry 74 corrects the brightness value Bn of the X-ray image relative to the latest index to the brightness value Cn of the calculation result.

At step ST80, the processing circuitry 74 causes an X-ray image having the corrected brightness value Cn on the display 72, and shifts to step ST90.

At step ST90, the processing circuitry 74 determines whether or not contrast imaging of the subject P's heart region has been complete; if not, the processing returns to step ST10.

Figure 7:
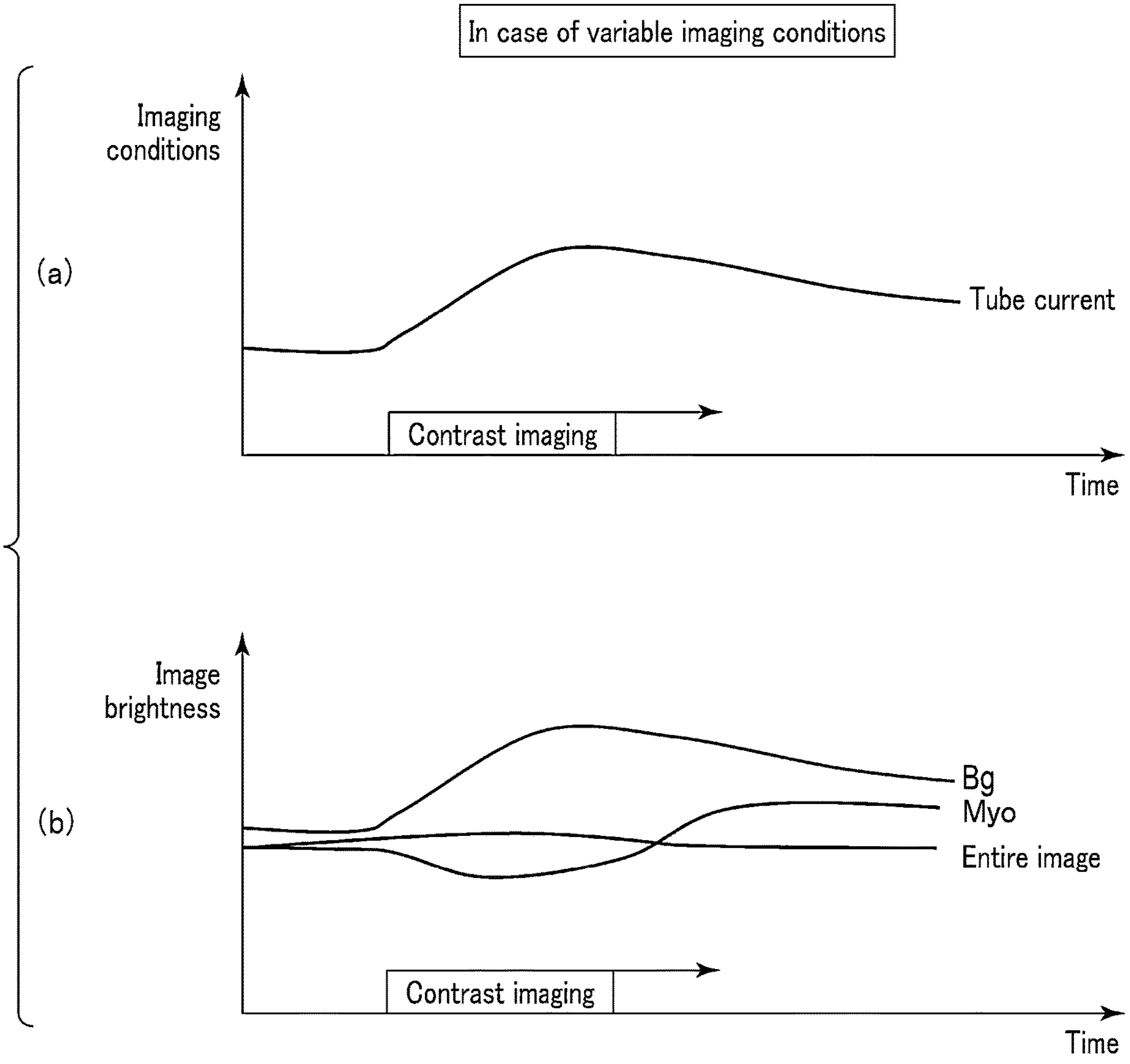
FIG. 7 is a schematic diagram for illustrating an image brightness in a case where imaging conditions change.

That is, if the automatic brightness control is in the on state, the X-ray diagnostic apparatus 1 repeatedly performs the operations from step ST10 to step ST30 and step ST50 to step ST80 via step ST90 during the contrast imaging in which the imaging conditions change. At steps ST10 to ST30, of the imaging conditions, the tube current increases as shown in FIG. 7(*a*), in accordance with the automatic brightness control. In accordance therewith, as shown in FIG. 7(*b*), the image brightness increases in each of the background region of interest Bg and the cardiac-muscle region of interest Myo, compared to the image brightness shown in FIG. 5, and the image brightness of the entire X-ray image runs substantially constant. The X-ray image having the image brightness shown in FIG. 7(*b*), which is a prior-to-correction image and is a normal clinical image obtained by brightening, through automatic brightness control, the entire X-ray image which has been darkened by injection of the contrast medium, is displayed on a part of the display 72. In such a prior-to-correction X-ray image, the image brightness of the background region of interest Bg, which the contrast medium does not reach, increases, as shown in FIG. 7(*b*), and it cannot be directly used for the image analysis.

Figure 8:
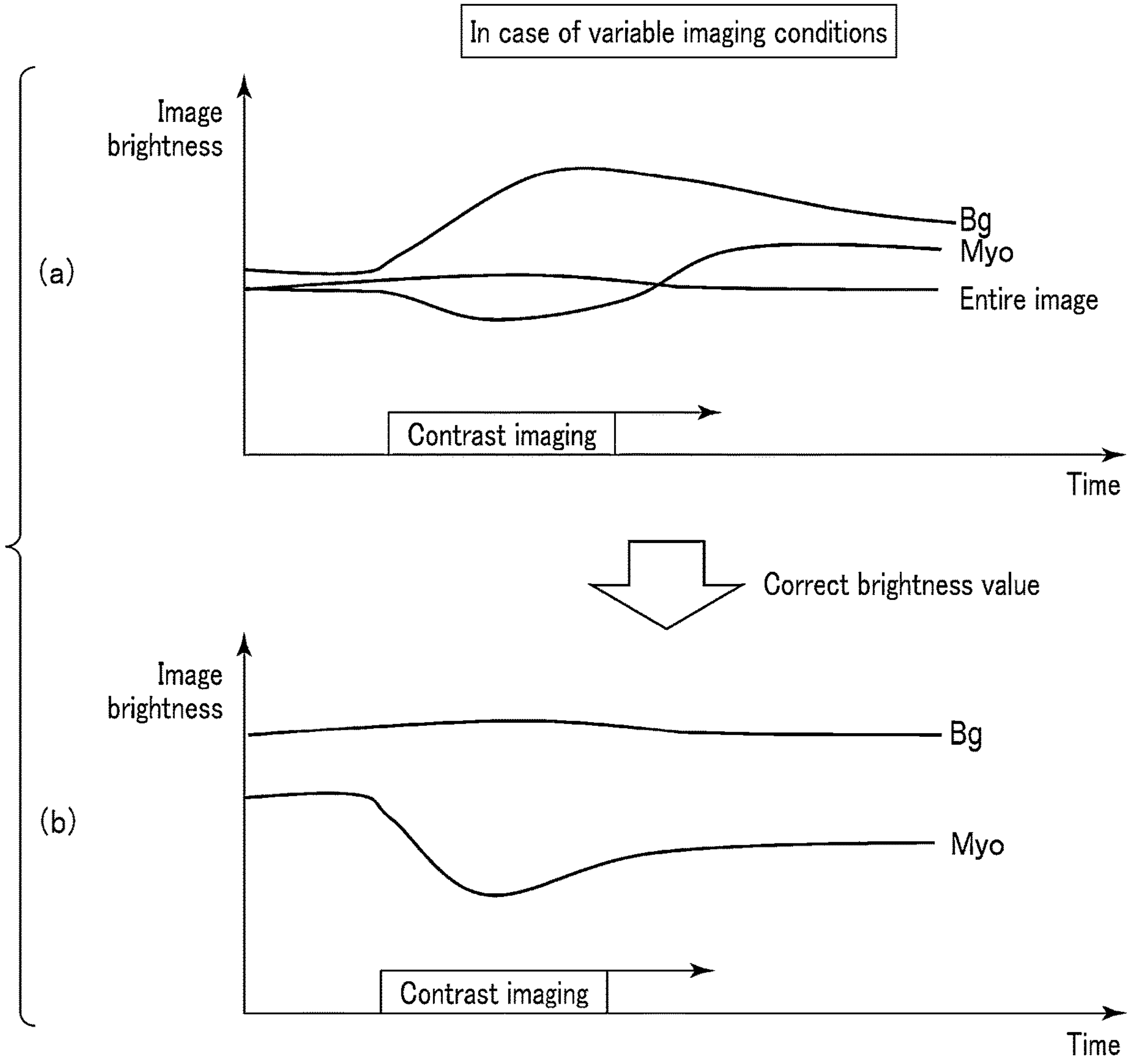
FIG. 8 is a schematic diagram for illustrating operations in the first embodiment.

On the other hand, at step ST70, the brightness value of the X-ray image relative to the latest imaging conditions after start of injection of the contrast medium as shown in FIG. 8(*a*) is corrected to the brightness value of the X-ray image relative to the reference imaging conditions prior to injection of the contrast medium as shown in FIG. 8(*b*). Note that the graph shown in FIG. 8(*a*) is identical to that shown in FIG. 7(*b*). In such a corrected X-ray image, the image brightness of the background region of interest Bg, which the contrast medium does not reach, runs substantially constant, as shown in FIG. 8(*b*), and it can be directly used for the image analysis. The X-ray image having the image brightness shown in FIG. 8(*b*) is displayed in another part of the display 72 at step ST80. For example, the corrected X-ray image may be displayed in a part of a peripheral region of the display 72. At this time, on the display 72, a first display region of the prior-to-correction X-ray image (normal clinical image) is located, for example, at substantially the center of the display 72, and has a broader area than the second display region of the corrected X-ray image. However, the configuration is not limited thereto, and the size and the arrangement of each of the first display region and the second display region may be suitably set. Display of the corrected X-ray image may be omitted.

On the other hand, after step ST80, if it is determined at step ST90 that the contrast imaging has been complete, the processing circuitry 74 completes the processing.

As described above, according to the first embodiment, the X-ray tube radiates X-rays toward a subject P into which a contrast medium is injected. The X-ray detector 13 is adapted to detect X-rays radiated by the X-ray tube and transmitted through the subject P. The processing circuitry 74 generates an X-ray image of the subject P based on an output from the X-ray detector 13. The processing circuitry 74 acquires indexes related to the brightness of the X-ray image. Of the acquired indexes, the processing circuitry 74 corrects, based on a reference index prior to injection of a contrast medium and a latest index after start of injection of the contrast medium, a brightness value of the X-ray image relative to the latest index. By the above-described configuration of correcting, based on the reference index and the latest index related to a brightness of the X-ray image, a brightness value of the X-ray image relative to the latest index, it is possible to suppress, in an image density change in a temporal direction of the X-ray image caused by the contrast medium, the effect caused by a change in imaging conditions.

Figure 9:
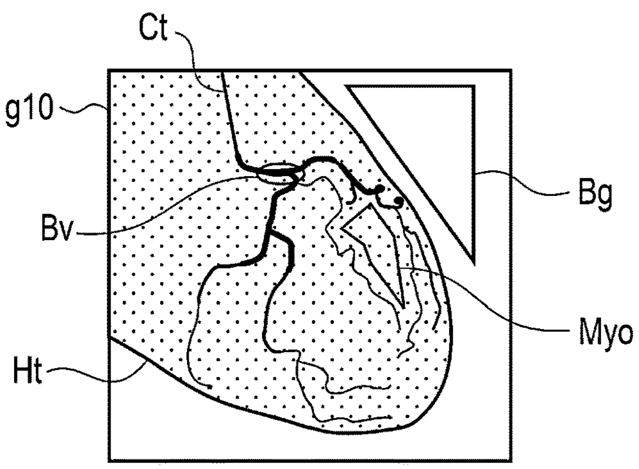
FIG. 9 is a schematic diagram for illustrating an effect of the first embodiment.
Figure 10:
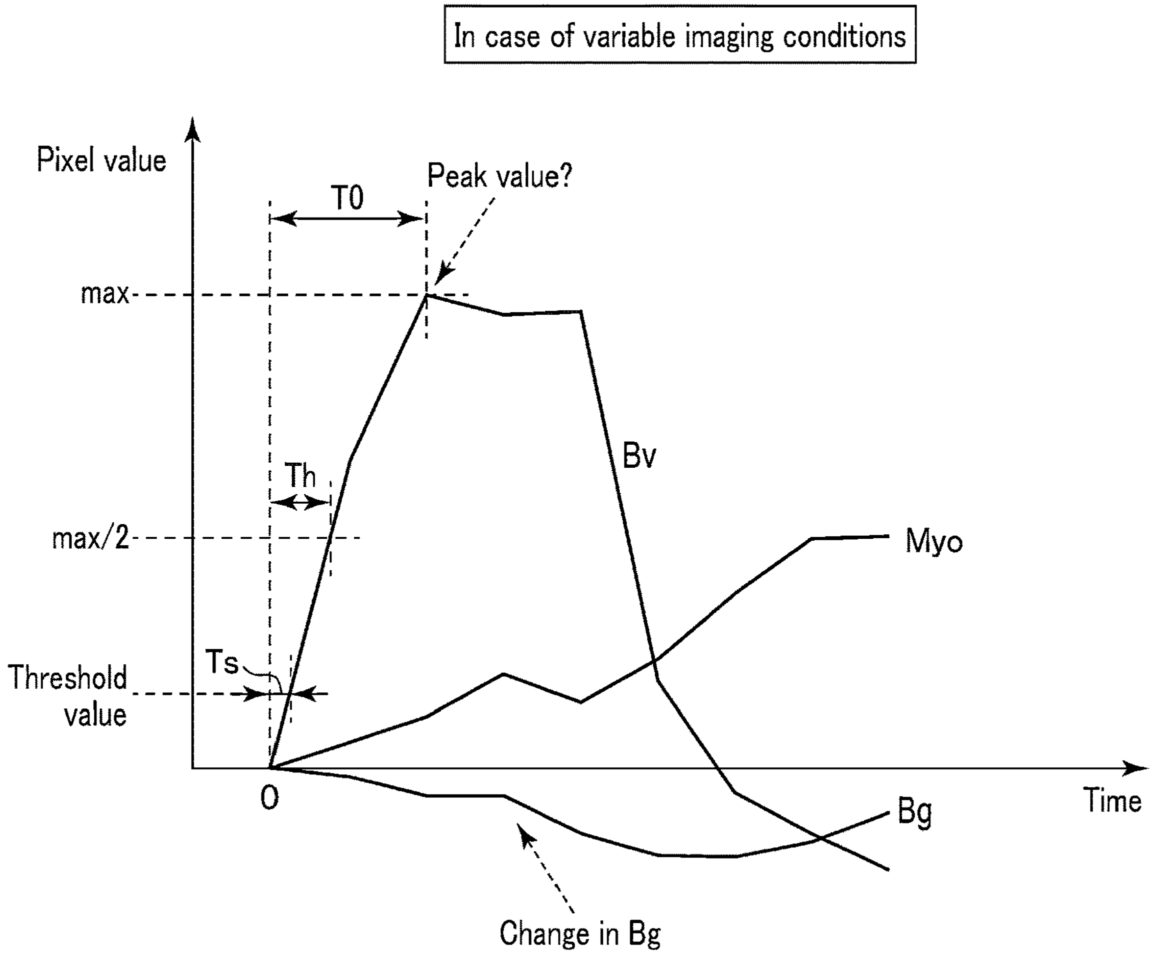
FIG. 10 is a schematic diagram for illustrating an effect of the first embodiment.

An additional explanation about this effect will be provided with reference to FIGS. 9 and 10. An X-ray image g10 shown in FIG. 9 is an example of a prior-to-correction image obtained at a middle stage of contrast imaging, of multiple-frame X-ray images obtained by the contrast imaging. It is assumed that, in the prior-to-correction X-ray image g10, a blood-vessel region of interest By and a cardiac-muscle region of interest Myo are set in a heart region Ht into which a catheter Ct is inserted. It is also assumed that, in the prior-to-correction X-ray image g10, a background region of interest Bg is set in a part of a background region different from the heart region Ht. By analyzing the prior-to-correction X-ray image for each frame, it is possible to obtain a time density curve in which the lateral axis represents time and the horizontal axis represents an average pixel value in each of the regions of interest Bv, Myo, and Bg, as shown in FIG. 10. In general, with a time density curve, it is possible to identify a feature amount related to a flow of a contrast medium. Examples of this type of feature amount include an inflow time of the contrast medium. Of several known methods for identifying the inflow time of the contrast medium, three methods will be described herein as typical examples. The first one is a method of identifying, for each pixel, a time T0 at which a peak value (a maximum value) of a time density curve occurs, which is also referred to as a "time-to-peak" (TTP), as the inflow time of the contrast medium. The second one is a method of identifying, for each pixel, a time Th at which ½ of the peak value of the time density curve is exceeded as the inflow time of the contrast medium. The third one is a method of identifying, for each pixel, a time Ts at which a certain threshold value of the time density curve is exceeded, which is also referred to as a "time-to-arrival" (TTA), as the inflow time of the contrast medium. Note that the feature amount related to the flow is not limited to the inflow time of the contrast medium, and may be, for example, a mean transit time (MTT) of the contrast medium. In FIG. 10, the times T0, Th, Ts can be read from the time density curve of the blood-vessel region of interest By based on the prior-to-correction multiple-frame X-ray images. In a normal time density curve, which is obtained on the premise that the imaging conditions do not change, the line (base line) of the background region of interest Bg, which the contrast medium does not reach, runs substantially constant. On the other hand, in the time density curve shown in FIG. 10, since the line (base line) of the background region of interest Bg, which the contrast medium does not reach, changes, it can be seen that a change in the imaging conditions is affected. There is thus a concern that, in the time density curve based on the prior-to-correction X-ray image, a rising shape, a peak value, etc. may be deviated, causing an error in the read times T0, Th, and Ts.

On the other hand, according to the first embodiment, with the configuration of correcting, based on a reference index and a latest index related to a brightness of an X-ray image, a brightness value of the X-ray image relative to the latest index, the image brightness of the background region of interest Bg runs substantially constant, as shown in FIG. 8(*b*). Accordingly, the time density curve (not illustrated) is not affected by a change in the imaging conditions based on the corrected X-ray image, and the line (base line) of the background region of interest Bg becomes substantially constant. It is thereby possible to suppress, in an image density change in the temporal direction of the X-ray image caused by the contrast medium, the effect caused by a change in the imaging conditions. Moreover, it is possible to obtain a correct time density curve of a contrast region such as a blood-vessel region of interest By and a cardiac-muscle region of interest Myo based on the corrected X-ray image, thus realizing the correct blood flow measurement.

Furthermore, according to the first embodiment, the processing circuitry 74 corrects the brightness value of the X-ray image relative to the latest index so as to maintain the brightness of the X-ray image relative to the reference index. In addition to the above-described effects, it is thereby possible, among the regions of the corrected X-ray image, to maintain the brightness of the background region which the contrast medium does not reach.

Moreover, according to the first embodiment, the processing circuitry 74 obtains a change ratio of the latest index relative to the reference index, and corrects a brightness value based on the change ratio. In addition to the above-described effects, it is thereby possible, among the regions of the corrected X-ray image, to suppress a change in brightness of the background region which the contrast medium does not reach.

Furthermore, according to the first embodiment, the processing circuitry 74 acquires imaging conditions of the X-ray image as indexes. It is thereby possible, in addition to the above-described effects, to acquire the indexes related to the brightness of the X-ray image without analyzing the X-ray image, by referring to the imaging conditions in the memory 71.

Moreover, according to the first embodiment, the processing circuitry 74 acquires a tube current-time product as one of the indexes. It is thereby possible, in addition to the above-described effects, to acquire the index without analyzing the X-ray image by referring to the tube current and the pulse width in the memory 71 or the tube current-time product in the memory 71.

Furthermore, according to the first embodiment, the processing circuitry 74 adjusts the imaging conditions of the X-ray image, thereby executing automatic brightness control of controlling the brightness of the X-ray image of the subject P. It is thereby possible, in addition to the above-described effects, to brighten the entire X-ray image, which has been darkened by injection of the contrast medium.

Moreover, according to the first embodiment, the processing circuitry 74 causes the display 72 to display an X-ray image with a corrected brightness value. It is thereby possible, in addition to the above-described effects, to visually confirm that the brightness value of the X-ray image has been corrected.

(Modification)

In the first embodiment, a brightness value of the X-ray image is corrected by executing steps ST50 to ST70 during contrast imaging; however, the configuration is not limited thereto. For example, after the completion of the contrast imaging, steps ST50 to ST70 may be executed based on the X-ray image and the imaging conditions of each frame stored in the memory 71, etc., and the brightness value of the X-ray image may be corrected by executing steps ST50 to ST70. Note that, in the case of correcting the brightness value after the completion of the contrast imaging, preliminary contrast imaging for setting a region of interest in advance may be omitted. In either case, according to the present modification, it is possible to obtain effects similar to those of the first embodiment.

Similarly, in the first embodiment, a prior-to-correction X-ray image and a corrected X-ray image are displayed during the contrast imaging; however, the configuration is not limited thereto. For example, only a prior-to-correction X-ray image may be displayed during the contrast imaging. With this modification, too, it is possible to obtain effects similar to those of the first embodiment.

Second Embodiment

The second embodiment differs from the first embodiment in which the imaging conditions are used as indexes, and is an embodiment in which brightness values of a background region of interest Bg, which the contrast medium does not reach, are acquired as indexes. The background region of interest Bg is an example of a background region which a contrast medium does not reach.

In accordance therewith, the acquiring function 745 of the processing circuitry 74 acquires a brightness value from a part of the X-ray image, instead of the imaging conditions in the above-described function. For example, the acquiring function 745 acquires, from the generated X-ray image, brightness values of the background region of interest Bg, which the contrast medium does not reach, as indexes. At this time, the acquiring function 745 may, for example, set the background region of interest Bg based on a plurality of X-ray images that have been generated. For example, the acquiring function 745 may generate a minimum-value image indicating a contrast region which the contrast medium has reached from each of the X-ray images, and set a background region of interest Bg based on the minimum-value image. That is, the acquiring function 745 sets a background region of interest Bg based on each minimum-value image, which temporarily changes, indicating a contrast region, and a region obtained by excluding the contrast region indicated by each minimum-value image from the X-ray image being a background region.

Also, the correcting function 746 uses the brightness values acquired by the acquiring function 745 as indexes in the above-described function.

The remaining aspects are the same as the first embodiment.

Figure 11:
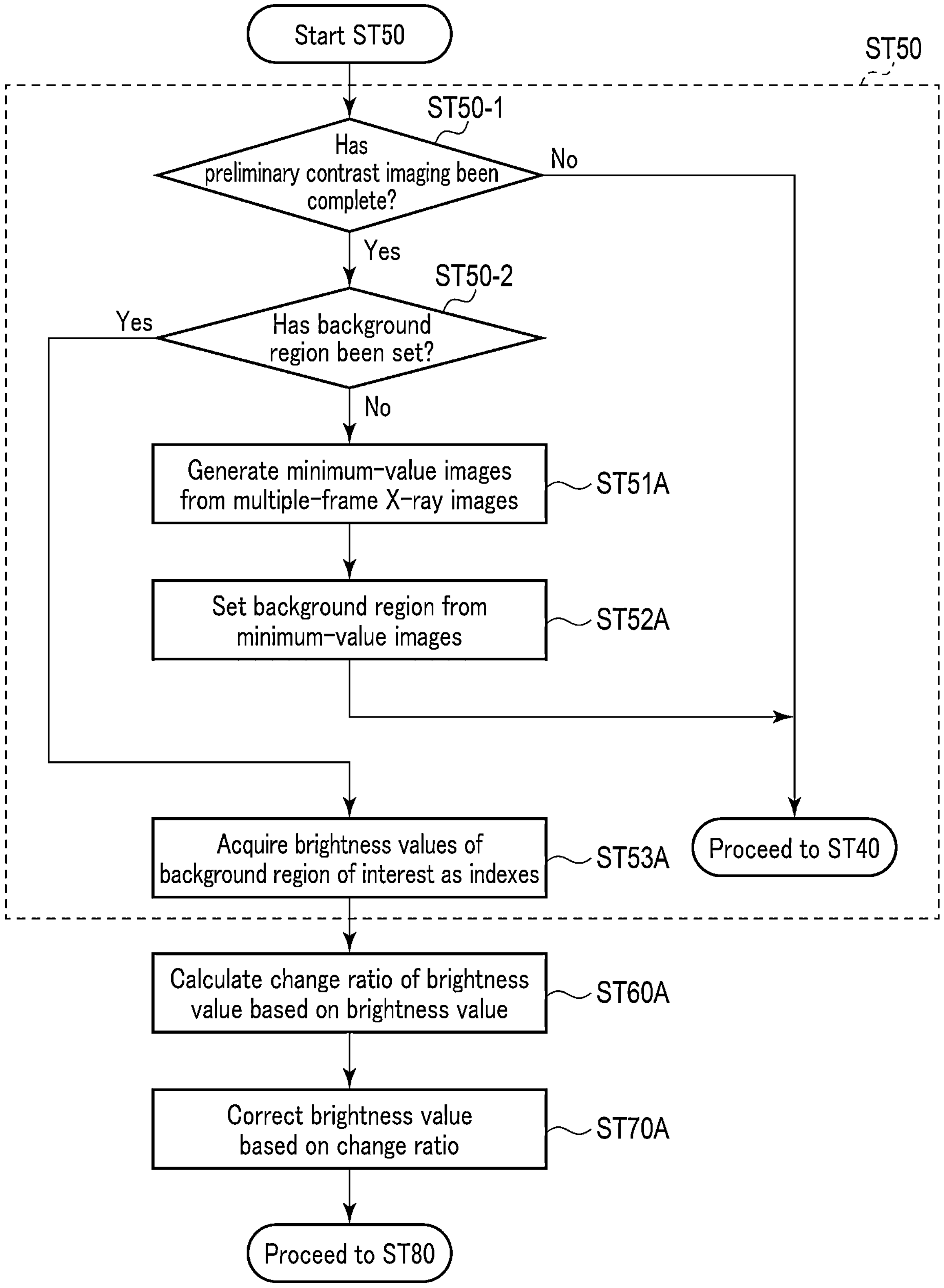
FIG. 11 is a flowchart for illustrating operations in a second embodiment.
Figure 12:
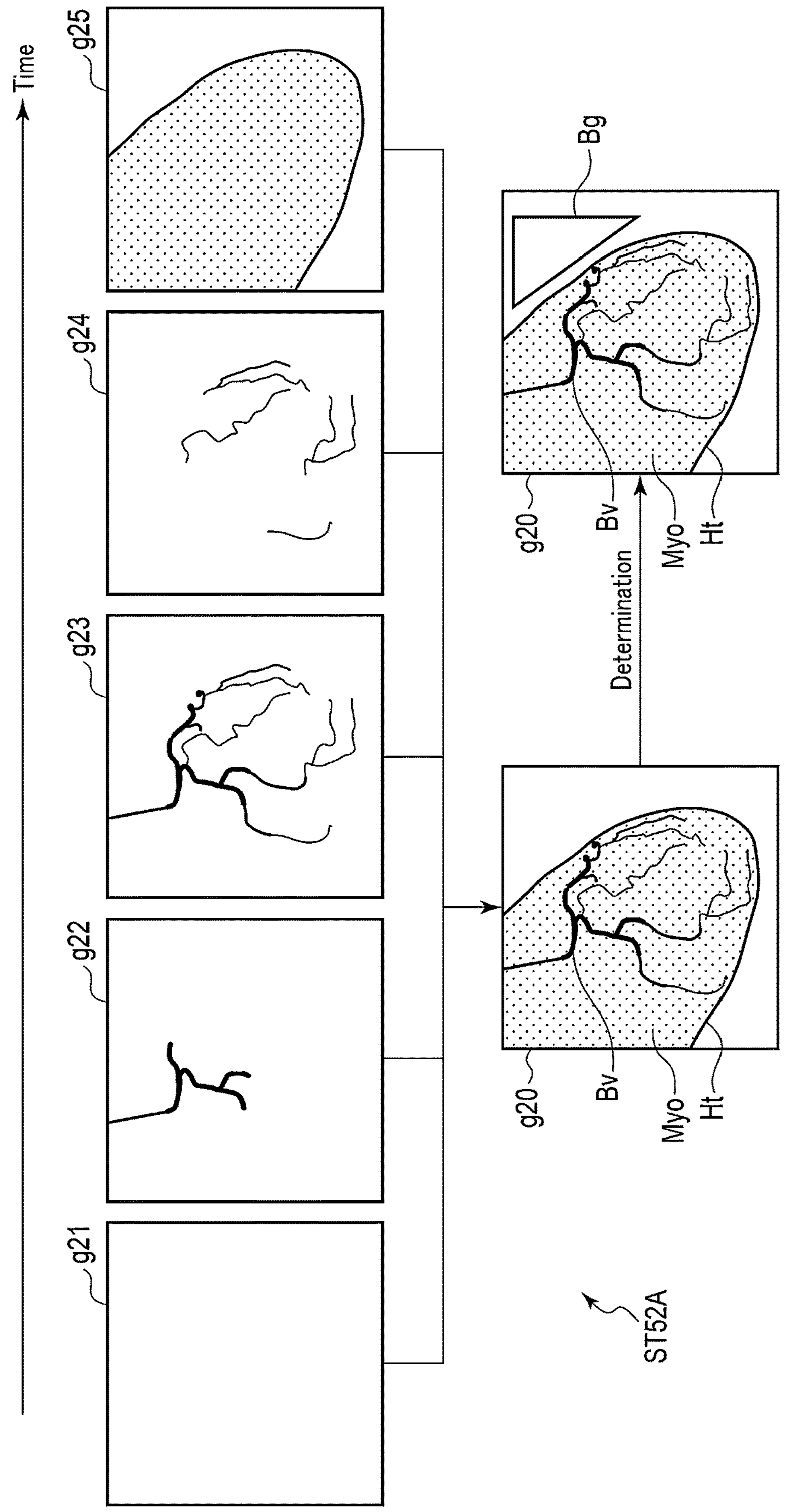
FIG. 12 is a schematic diagram for illustrating operations in the second embodiment.
Figure 13:
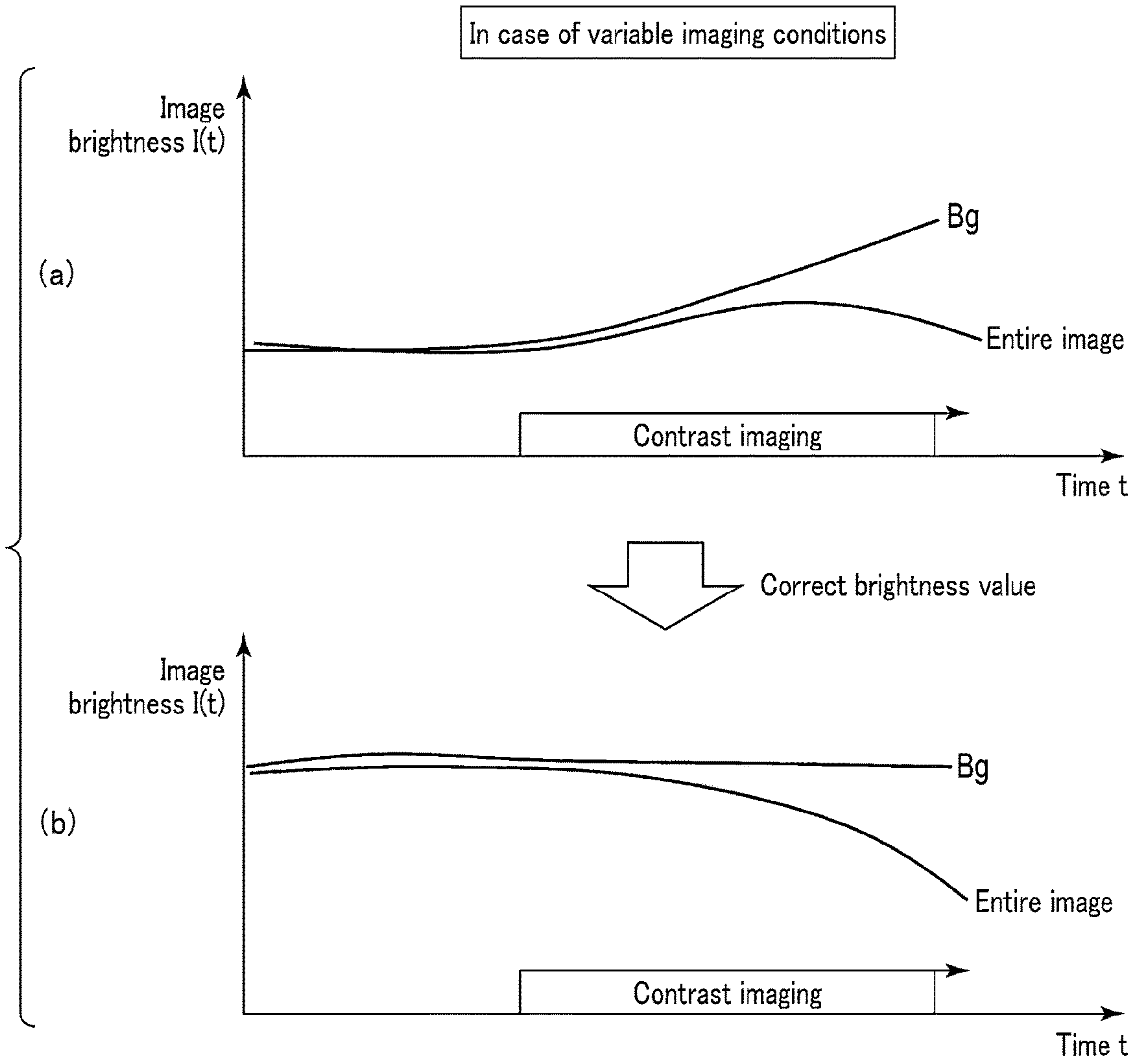
FIG. 13 is a schematic diagram for illustrating operations in the second embodiment.

Next, operations according to the second embodiment will be described with reference to FIGS. 11 to 13. FIG. 11 shows a flowchart, and FIGS. 12 and 13 show schematic diagrams. In the second embodiment, after low-dose preliminary contrast imaging for automatically setting a background region, main contrast imaging for performing image analysis including creation of a time density curve is performed. In the second embodiment, in addition to steps ST10 to ST40, ST80, and ST90 as described above, steps ST50, ST60A, and ST70A are performed between step ST30 and ST80, as shown in FIG. 11. These steps will be described in sequence.

At step ST50, the processing circuitry 74 sets, after the preliminary contrast imaging, for example, a background region of interest Bg prior to starting the main contrast imaging, and acquires, from the background region of interest Bg, indexes related to brightness of the X-ray image in the main contrast imaging. Step ST50 includes steps ST50-1, ST50-2 and ST51-A to ST53A, as shown, for example, in FIG. 11. That is, upon determining whether or not the preliminary contrast imaging has been complete (ST50-1), the processing circuitry 74 shifts to step ST40 if the preliminary contrast imaging has not been complete, and determines whether a background region has been set if the preliminary contrast imaging has been complete (ST50-2). If it is determined at step ST50-2 that the background region has not been set, the processing shifts to step ST51A, and if it is determined that the background region has been set, the processing shifts to step ST53A.

At step ST51A, the processing circuitry 74 generates a plurality of minimum-value images from multiple-frame X-ray images. Note that each minimum-value image is generated from a single-frame X-ray image. Each minimum-value image indicates, in each X-ray image, a contrast region such as a blood vessel region or a cardiac muscle region which the contrast medium has reached. Also, the processing circuitry 74 sets a background region from the plurality of minimum-value images (ST52A). As shown in FIG. 12, for example, the processing circuitry 74 synthesizes the minimum-value images g21, . . . , g22, . . . , g23, . . . , g24, . . . , g25, and . . . , and generates a synthesis image g20 including a heart region Ht equivalent to the contrast region. The processing circuitry 74 determines a region other than the heart region Ht in the synthesis image g20, and sets a background region of interest Bg based on the determination result as a background region. In accordance with an operation of the input interface 73 by the operator, the processing circuitry 74 sets a blood-vessel region of interest By in a part of the blood vessel region, and sets a cardiac-muscle region of interest Myo in a part of the cardiac muscle region. Thereby, step ST52A is complete, and step ST53A can be performed in the main contrast imaging.

At step ST53A, the processing circuitry 74 acquires brightness values of the background region of interest Bg as indexes Id0 and Idn (ST53A).

At this time, the brightness value I(t) of the background region of interest Bg is acquired as a value that varies according to a time t. Assuming, for example, that, in the main contrast imaging, the time prior to the contrast medium injection is time t1 and a given time during the contrast imaging after the start of injection is time t2, the brightness values I(t1) and I(t2) of the background region of interest Bg are ideally expressed by the following formulae (1) and (2). The brightness value I(t1) corresponds to the reference index Id0, and the brightness value I(t2) corresponds to the latest index Idn.

$$I(t1) = Io * \exp(-\mu * L) \tag{1}$$

$$I(t2) = k * Io * \exp(-\mu * L) \tag{2}$$

Here, Io represents a brightness value in the absence of the subject P, p represents a linear absorption coefficient, L represents a body thickness of the subject P, and k represents a change ratio.

If the imaging conditions are constant, since the change ratio k is 1, k=1 and I(t1)=I(t2) are satisfied, and the image brightness becomes constant. If the imaging conditions change, the brightness values I(t1) and I(t2) of the background region of interest Bg, which the contrast medium does not reach and the linear absorption coefficient μ does not change over time, are acquired as indexes. Step ST50 is complete upon performing such steps.

At step ST60A, of the acquired indexes, the processing circuitry 74 calculates, based on the reference index prior to injection of the contrast medium and the latest index after start of injection of the contrast medium, a change ratio of the latest index to the reference index. Note that the acquired indexes are the brightness values I(t1) and I(t2) of the background region of interest Bg. Accordingly, the change ratio k is calculated from the formula of k=I(t2)/I(t1) as a brightness value ratio. Also, the change ratio k is updated to a value that varies according to the change of the latest brightness value I(t2) in the background region of interest Bg for each frame of the X-ray image.

At step ST70A, the processing circuitry 74 corrects the brightness value I(t2) of the X-ray image relative to the latest index Idn based on the change ratio, similarly to step ST70. The corrected brightness value Ic(t2) becomes 1/k times the prior-to-correction brightness value I(t2), as shown in the following formula (3).

$$Ic(t2) = I(t2)/k = Io * \exp(-\mu * L) \tag{3}$$

The corrected brightness value Ic(t2) of the background region of interest Bg, for which the linear absorption coefficient μ does not change over time, is equal to the brightness value I(t1) prior to the contrast medium injection. The corrected brightness value Ic(t2) of the blood-vessel region of interest Bv, for which the linear absorption coefficient μ increases according to how far the contrast medium reaches, becomes smaller than the brightness value I(t1) prior to the contrast medium injection. Similarly, the corrected brightness value Ic(t2) of the cardiac-muscle region of interest Myo becomes smaller than the brightness value I(t1) prior to the contrast medium injection according to how far the contrast medium reaches. Thereby, the brightness of the overall X-ray image decreases.

That is, at step ST70A, the brightness value of the prior-to-correction X-ray image relative to the latest index prior to the start of injection of the contrast medium, as shown in FIG. 13(*a*), is corrected to the brightness value of the X-ray image relative to the reference index prior to the injection of the contrast medium, as shown in FIG. 13(*b*). In such a corrected X-ray image, the image brightness of the background region of interest Bg, which the contrast medium does not reach, runs substantially constant, as shown in FIG. 13(*b*), and it can be directly used for the image analysis.

Similarly, the processing of step ST80 and thereafter is performed.

As described above, according to the second embodiment, the processing circuitry 74 acquires, from the generated X-ray image, brightness values of a background region of interest Bg, which a contrast medium does not reach, as indexes. Since brightness values directly indicating the brightness of the X-ray image are acquired as indexes, it is possible, in addition to the effects of the first embodiment, to maintain the corrected brightness value at a constant value reliably, compared to the imaging conditions in which the brightness of the X-ray image is indirectly indicated.

Also, according to the second embodiment, a brightness value of a region of the entire X-ray image which the contrast medium does not reach (a region other than the heart region Ht), is acquired, and the brightness of the entire X-ray image is corrected in the time direction to make the temporal change of the brightness value of the region which the contrast medium does not reach constant. It is thereby possible to suppress, in the change in brightness value of the entire X-ray image in the temporal direction during the contrast imaging, the effect caused by a change in the imaging conditions.

Also, according to the second embodiment, the processing circuitry 74 sets a background region of interest Bg based on a plurality of X-ray images that have been generated. It is thereby possible, in addition to the above-described effects, to improve the precision in the background region of interest Bg in accordance with the number of X-ray images, while saving the labor of setting a background partial region Bg. At each time during the contrast imaging, a region which the contrast medium does not reach varies from frame to frame of the X-ray image. On the other hand, it is necessary that the background region of interest Bg in all the X-ray images during the contrast imaging be a region which the contrast medium does not reach. It is therefore preferable, from the viewpoint of preciseness, to set the background region of interest Bg based on multiple-frame X-ray images.

According to the second embodiment, the processing circuitry 74 generates, from each of the X-ray images, a minimum-value image indicating a contrast region which the contrast medium has reached, and sets a background region of interest Bg based on the minimum-value image. It is thereby possible, in addition to the above-described effects, to improve precision in the background region of interest Bg according to the number of X-ray images used for generation of the minimum-value images. In addition, by setting the background region of interest Bg based on the minimum-value images, there is no concern that the operator may incorrectly set the background region of interest Bg to include a part of the contrast region, and it is possible to ensure reliability of the background region of interest Bg.

(Modification)

In the second embodiment, a background region of interest Bg is set based on each minimum-value image. On the other hand, in the modification of the second embodiment, a background region of interest Bg is set based on a change in a brightness value of each region in an X-ray image, as shown in FIG. 4. The background region of interest Bg is an example of a background region which a contrast medium does not reach.

In accordance therewith, the acquiring function 745 of the processing circuitry 74 specifies, with the above-described function, a region with a substantially constant brightness value from the plurality of X-ray images, and sets a part of the specified region as a background region of interest Bg.

The remaining aspects are the same as the second embodiment.

Figure 14:
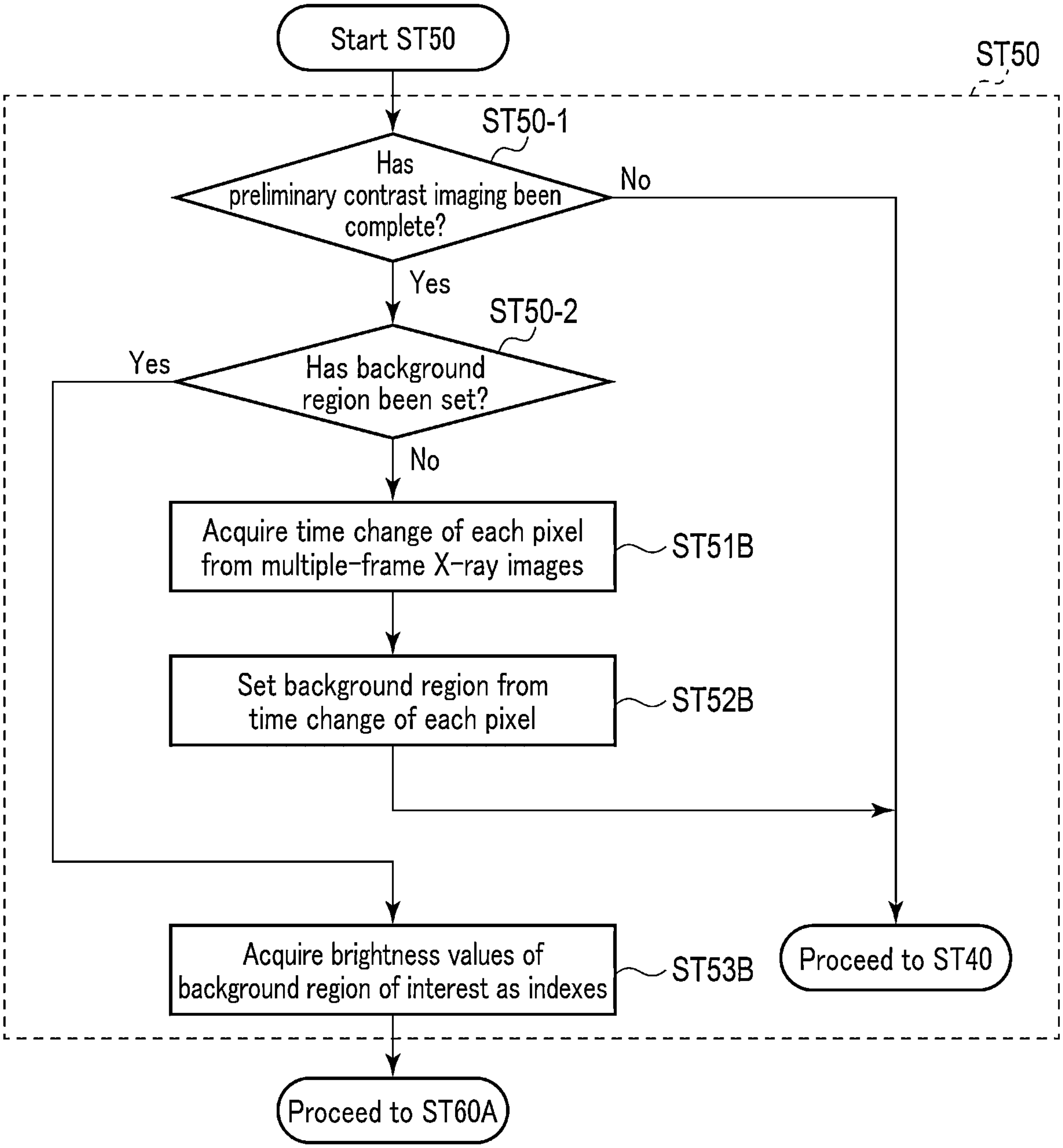
FIG. 14 is a flowchart for illustrating operations in a modification of the second embodiment.

With the above-described configuration, in addition to steps ST10 to ST40 and ST60A to ST90 as described in the second embodiment, step ST50 is executed between steps ST30 and ST60A, as shown in FIG. 14. Step ST50 shown in FIG. 14 differs from that shown in FIG. 11 in terms of steps ST51B and ST52B, related to acquisition of a background region. These steps will be described in sequence.

At step ST50, the processing circuitry 74 performs determinations at steps ST50-1 and ST50-2 as described above.

If it is determined at step ST50-2 that the background region has not been set, the processing shifts to step ST51B, and if it is determined that the background region has been set, the processing shifts to step ST53B.

At step ST51B, the processing circuitry 74 acquires a time change in brightness value of each pixel from multiple-frame X-ray images. Also, the processing circuitry 74 sets a background region from the time change in brightness value of each pixel (ST52B). The processing circuitry 74 specifies a region in which a time change in brightness value of each pixel is substantially constant from the multiple-frame X-ray images, and sets a background region of interest Bg, which is a part of the specified region, as a background region, as shown, for example, in FIG. 4. Thereby, step ST52B is complete, allowing step ST53B to be performed.

At step ST53B, the processing circuitry 74 acquires brightness values of the background region of interest Bg as indexes. At this time, a brightness value I(t) of the background region of interest Bg is acquired as a value that varies according to a time t, similarly to the second embodiment.

After that, the processing of step ST60A and thereafter is performed, similarly to the second embodiment.

Thus, according to the modification of the second embodiment, the processing circuitry 74 specifies a region with a substantially constant brightness value from a plurality of X-ray images, and sets a part of the specified region as a background region of interest Bg. It is thereby possible to obtain effects similar to those of the second embodiment, while eliminating the load of generating the minimum-value images g21 to g25 and the synthesis image g20.

In the second embodiment and its modification, a brightness value of the X-ray image is corrected by executing steps ST50 to ST70 during contrast imaging including preliminary contrast imaging and main contrast imaging; however, the configuration is not limited thereto. For example, the preliminary contrast imaging for setting a background region may be omitted, and after the completion of contrast imaging, the brightness value of the X-ray image may be corrected by executing steps ST50 to ST70 based on the multiple-frame X-ray images stored in the memory 71, etc. In this case, steps ST50-1 and ST50-2 of step ST50, which are related to determination of completion of the preliminary contrast imaging and determination of setting of the background region, are omitted. With this modification, too, it is possible to obtain effects similar to those of the second embodiment and its modification.

Similarly, in the second embodiment and its modification, step ST80 in which a prior-to-correction X-ray image and a corrected X-ray image are displayed during the contrast imaging is performed; however, the configuration is not limited thereto. For example, at ST80, only a prior-to-correction X-ray image may be displayed during the contrast imaging. With this modification, too, it is possible to obtain effects similar to those of the second embodiment and its modification.

According to at least one embodiment described above, it is possible to suppress, in the image density change of the X-ray image in the temporal direction caused by the contrast medium, the effect caused by a change in the imaging conditions.

The term "processor" used in the descriptions of the embodiments means, for example, a central processing unit (CPU), a graphics processing unit (GPU), or a circuit such as an application-specific integrated circuit (ASIC), a programmable logic device (e.g., simple programmable logic device (SPLD), a complex programmable logic device (CPLD), and a field programmable gate array (FPGA)). If, for example, the processor is a CPU, the processor reads and executes programs stored in storage circuitry to realize corresponding functions. On the other hand, if the processor is an ASIC, the function is directly incorporated as a logic circuit into the circuit of the processor, instead of the program being stored in the storage circuitry. The embodiments herein do not limit each processor to a single circuitry-type processor, and multiple independent circuits may be combined and integrated as a single processor to realize the intended functions. Furthermore, a plurality of structural components shown in FIG. 1 may be integrated into a single processor to realize the functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
an X-ray tube configured to radiate X-rays toward a subject into which a contrast medium is injected;
an X-ray detector configured to detect the X-rays radiated by the X-ray tube and transmitted through the subject; and
processing circuitry configured to:
generate an X-ray image based on an output from the X-ray detector;
acquire indexes related to a brightness of the X-ray image; and
correct, based on a reference index prior to injection of the contrast medium and a latest index after start of the injection of the contrast medium, a brightness value of the X-ray image relative to the latest index, the reference index and the latest index being included in the acquired indexes.

2. The X-ray diagnostic apparatus according to claim 1, wherein
the processing circuitry is configured to correct the brightness value so as to maintain the brightness of the X-ray image relative to the reference index.

3. The X-ray diagnostic apparatus according to claim 2, wherein
the processing circuitry is configured to obtain a change ratio of the latest index to the reference index, and correct the brightness value based on the change ratio.

4. The X-ray diagnostic apparatus according to claim 1, wherein
the processing circuitry is configured to acquire imaging conditions of the X-ray image as the indexes.

5. The X-ray diagnostic apparatus according to claim 1, wherein
the processing circuitry is configured to acquire a tube current-time product as one of the indexes.

6. The X-ray diagnostic apparatus according to claim 1, wherein
the processing circuitry is configured to acquire, from the generated X-ray image, brightness values of a background region which the contrast medium does not reach, as the indexes.

7. The X-ray diagnostic apparatus according to claim 6, wherein the processing circuitry is configured to set the background region based on a plurality of X-ray images generated based on the output from the X-ray detector.

8. The X-ray diagnostic apparatus according to claim 7, wherein the processing circuitry is configured to generate, from each of the plurality of X-ray images, a minimum-value image indicating a contrast region which the contrast medium has reached, and to set the background region based on the minimum-value image.

9. The X-ray diagnostic apparatus according to claim 7, wherein the processing circuitry is configured to specify a region with a substantially constant brightness value from the plurality of X-ray images, and to set a part of the specified region as the background region.

10. The X-ray diagnostic apparatus according to claim 1, wherein the processing circuitry is further configured to perform automatic brightness control of controlling the brightness of the X-ray image of the subject through adjusting imaging conditions of the X-ray image.

11. The X-ray diagnostic apparatus according to claim 1, wherein the processing circuitry is further configured to cause a display to display an X-ray image with a corrected brightness value.

12. A correction method, comprising:

radiating X-rays toward a subject into which a contrast medium is injected;

detecting the X-rays radiated and transmitted through the subject;

generating at least one X-ray image of the subject based on a result of the detecting of the X-rays;

acquiring indexes related to a brightness of the X-ray image; and correcting, based on a reference index prior to injection of the contrast medium and a latest index after start of the injection of the contrast medium, a brightness value of the X-ray image relative to the latest index, the reference index and the latest index being included in the acquired indexes.

* * * * *